(12) United States Patent
Kwan et al.

(10) Patent No.: US 6,187,047 B1
(45) Date of Patent: Feb. 13, 2001

(54) BONE GRAFTING MATRIX

(75) Inventors: Michael K. Kwan, Cupertino; Stephen D. Pacetti, Sunnyvale; Ronald K. Yamamoto, San Francisco, all of CA (US)

(73) Assignee: Orquest, Inc., Mountain View, CA (US)

( * ) Notice: Under 35 U.S.C. 154(b), the term of this patent shall be extended for 0 days.

(21) Appl. No.: 09/110,726

(22) Filed: Jul. 7, 1998

Related U.S. Application Data

(62) Division of application No. 08/633,554, filed on Apr. 17, 1996, now Pat. No. 5,776,193.
(60) Provisional application No. 60/005,523, filed on Oct. 16, 1995.

(51) Int. Cl.[7] .............................. A61F 2/28; A61K 27/24; A61K 27/12
(52) U.S. Cl. ................................. 623/16.11; 623/23.75; 623/23.56; 623/23.61
(58) Field of Search .............................. 623/16, 18, 11, 623/66, 901, 16.11, 23.75, 23.61, 23.56; 424/426

(56) References Cited

U.S. PATENT DOCUMENTS

| | | | |
|---|---|---|---|
| 4,294,753 | 10/1981 | Urist | 260/112 R |
| 4,434,094 | 2/1984 | Seyedin et al. | 260/112 R |
| 4,440,750 | 4/1984 | Glowacki et al. | 424/95 |
| 4,455,256 | 6/1984 | Urist | 260/112 R |
| 4,563,350 | 1/1986 | Nathan et al. | 424/95 |
| 4,627,982 | 12/1986 | Seyedin et al. | 424/95 |
| 4,698,326 | 10/1987 | Sauk et al. | 514/7 |
| 4,780,450 | 10/1988 | Sauk et al. | 514/2 |
| 4,789,663 | 12/1988 | Wallace et al. | 514/21 |
| 4,795,467 | 1/1989 | Piez et al. | 623/16 |
| 4,863,732 | 9/1989 | Nathan et al. | 424/95 |
| 4,888,366 | 12/1989 | Chu et al. | 523/115 |
| 4,962,091 | 10/1990 | Eppstein et al. | 514/2 |
| 5,092,883 | 3/1992 | Eppley et al. | 623/11 |
| 5,133,755 | 7/1992 | Brekke | 623/16 |
| 5,208,219 | 5/1993 | Ogawa et al. | 514/12 |
| 5,231,169 | 7/1993 | Constantz et al. | 530/356 |
| 5,236,456 | 8/1993 | O'Leary et al. | 623/16 |
| 5,264,214 | 11/1993 | Rhee et al. | 424/422 |
| 5,294,446 | 3/1994 | Schlameus et al. | 424/489 |
| 5,306,303 | 4/1994 | Lynch | 623/16 |
| 5,306,311 | 4/1994 | Stone et al. | 623/18 |
| 5,314,474 | 5/1994 | Helms et al. | 623/16 |
| 5,328,955 | 7/1994 | Rhee et al. | 525/54.1 |
| 5,338,772 | 8/1994 | Bauer et al. | 523/115 |
| 5,376,636 | 12/1994 | Rutherford et al. | 514/12 |
| 5,393,739 | 2/1995 | Bentz et al. | 514/12 |
| 5,397,770 | 3/1995 | Levin et al. | 514/2 |
| 5,413,989 | 5/1995 | Ogawa et al. | 514/12 |

FOREIGN PATENT DOCUMENTS

| | | | |
|---|---|---|---|
| 1 271 763 | 4/1970 | (GB) | C07Q/7/00 |
| WO 89/04646 | 6/1989 | (WO) | A61F/2/28 |
| WO 90/01955 | 3/1990 | (WO) | A61L/27/00 |
| WO 90/10018 | 9/1990 | (WO) | C07K/15/00 |
| WO 91/18558 | 12/1991 | (WO) | A61F/2/28 |
| WO 92/20371 | 11/1992 | (WO) | A61K/37/36 |
| WO 93/04710 | 3/1993 | (WO) | A61L/25/00 |
| WO 93/05808 | 4/1993 | (WO) | A61L/25/00 |
| WO 93/05823 | 4/1993 | (WO) | A61L/27/00 |
| WO 94/00145 | 1/1994 | (WO) | A61K/37/02 |
| WO 94/15653 | 7/1994 | (WO) | A61L/27/00 |
| WO 95/08304 | 3/1995 | (WO) | A61F/2/02 |

*Primary Examiner*—David J. Isabella
*Assistant Examiner*—Choon P. Koh
(74) *Attorney, Agent, or Firm*—Fish & Richardson, PC

(57) ABSTRACT

A porous three-dimensional bone grafting matrix is provided which is biodegradable. The matrix is preferably formed from mineralized collagen where the mineral comprises particulate calcium phosphate immobilized in the matrix and having a particle size of 5 microns or less.

8 Claims, No Drawings

BONE GRAFTING MATRIX

This is a divisional of U.S. application Ser. No. 08/633,554, filed Apr. 17, 1996 now U.S. Pat. No. 5,776,193.

The priority is claimed of U.S. provisional application Ser. No. 60/005,523, filed Oct. 16, 1995.

BACKGROUND

The invention relates to materials useful for bone repair.

There has been a number of materials studied to initiate bone repair and/or to restore or replace missing bone to address the problem of stimulating formation of bone at specific sites.

Among the approaches used to address this problem is a conformational method whereby an implant material, usually made of metal ceramic or other inorganic material in a form intended to mimic the form of the missing bone, is inserted into the site in which bone replacement is required. There is a risk that the host will reject the material or there will be a failure of integration of the implant with normal skeletal tissue. Some ceramic materials such as ceramic tricalcium phosphate, although acceptably biocompatible with the host and bone, when used as an implant, appear to lack sufficient mechanical properties of bone for general utility and the bone does not consistently grow into and become incorporated within the implant.

Another approach involves substituting the missing bone tissue with a matrix which functions as a support into which the new bone growth can occur. The theory is that the matrix attracts the cells committed to an osteogenic pathway and the new bone grows in and through the matrix by the process referred to as osteoconduction. Allogeneic bone (non-host bone) grafts are used for this method, however there is a substantially high failure rate. Even when the allogeneic bone grafts are accepted by the host, healing periods for consolidation and capacity for mechanical stress are of comparatively long duration compared to autogeneic bone (host-bone) grafting. The use of allogeneic bone also presents the issue of transmissible viral agents.

A third method involves the process known as osteoinduction, which occurs when a material induces the growth of new bone from the host's undifferentiated cells or tissues, usually around a temporary matrix. A number of compounds are shown to have such a capacity. See for example, U.S. Pat. No. 4,440,750 to Glowacki, U.S., Pat. Nos. 4,294,753 and 4,455,256 to Urist and U.S. Pat. Nos. 4,434,094 and 4,627,982 to Seyedin et al. The most effective of these compounds appear to be proteins which stimulate osteogenesis. However, when synthesized from natural sources they are present in extremely low concentrations and require large amounts of starting material to obtain even a minute amount of material for experimentation. The availability of such proteins by recombinant methods may eventually make the use of such proteins per se of more practical value. However, such proteins will probably still need to be delivered to the desired site in an appropriate matrix.

There have been compositions disclosed containing collagen and various forms of calcium phosphate directed to healing and bone growth.

U.S. Pat. No. 5,338,772 to Bauer et al. discloses a composite material containing calcium phosphate ceramic particles and a bio-absorbable polymer where the calcium phosphate ceramic is at least 50% by weight and the particles are joined by polymer bridges. The calcium phosphate ceramic particles are disclosed as having a size of about 20 microns to about 5 mm.

U.S. Pat. No. 4,795,467 to Piez et al. discloses a composition comprising calcium phosphate mineral particles admixed with atelopeptide reconstituted fibrillar collagen. The calcium phosphate mineral particles are disclosed as having a size in the range of 100–2,000 microns.

U.S. Pat. No. 4,780,450 to Sauk et al. discloses a composition for bone repair comprising particulate polycrystalline calcium phosphate ceramic, a phosphophorin calcium salt and a type I collagen in a weight ratio of 775–15:3–0.1:1. The ceramic particles are disclosed as being dense hydroxyapatite about 1 to 10 microns in diameter or larger dense hydroxy apatite ceramic particles of greater than about 100 microns in diameter.

PCT Application WO 94/15653 to Ammann et al. discloses formulations comprising tricalcium phosphate (TCP), TGF-$\beta$ and, optionally, collagen. The TCP is disclosed as being a delivery vehicle for the TGF-$\beta$ such that the TCP is of the particle size greater than 5 microns and preferably greater than about 75 microns. The most preferred range for the size of the TCP granules is disclosed as being 125–250 microns.

PCT Application WO 95/08304 discloses polymineralic precursor particles of hydroxyapatite mixed with insoluble collagen. The particle size of the polymineralic precursor particles are in the range from 0.5 microns to 5 microns. The precursor minerals are converted to hydroxyapatite by hydrolysis, and this process, it is believed, fuses the mineral to form monolithic hydroxyapatite.

British Patent Specification 1,271,763 to FMC Corporation discloses complexes of calcium phosphate and collagen.

SUMMARY OF THE INVENTION

A bone grafting matrix is provided which is porous and maintains structural integrity and porosity after implant for a period sufficient to augment the bone replacement process. The matrix comprises mineralized fibrillar insoluble collagen, collagen derivative or modified gelatin, bound with a binder. The minerals comprise particulate calcium phosphate immobilized within the matrix and having a particle size less than about 5 microns. The resulting product is lyophilized, cross-linked, dried and sterilized to form a porous matrix. The matrix may be used as a grafting material and/or a delivery vehicle for osteogenic growth factor. The matrix may be mixed with autogenous bone marrow and implanted for bone regeneration.

DESCRIPTION OF THE SPECIFIC EMBODIMENTS

The bone grafting matrix is produced using a water-insoluble biodegradable collagen, collagen derivative or modified gelatin. The gelatin will be modified to be insoluble in aqueous environments. The collagen may come from mineralized or unmineralized collagen sources, usually unmineralized collagen sources. Thus, the collagen may come from bone, tendons, skin, or the like, preferably Type I collagen which involves a combination of two strands of $\alpha_2$ and one $\alpha_1$ collagen chains. The collagen may be from a young source, e.g., calf, or a mature source, e.g., cow of two or more years. The source of the collagen may be any convenient animal source, mammalian or avian, and may include bovine, porcine, equine, chicken, turkey, or other domestic source of collagen. The insoluble collagenous tissue which is employed will normally be dispersed in a medium at an elevated pH, using at least about pH 8, more usually about pH 11–12. Commonly, sodium hydroxide is employed, although other hydroxides may be used, such as other alkali metal hydroxides or ammonium hydroxide.

Native collagen may be utilized in accordance with the present invention. Native collagen contains regions at each end which do not have the triplet glycine sequence. These regions (the telopeptides) are thought to be responsible for the immunogenicity associated with most collagen preparations. The immunogenicity can be mitigated by the removal of these regions to produce atelopeptide-collagen by digestion with proteolytic enzymes, such as trypsin and pepsin.

The concentration of collagen for mineralization will generally be in the range of about 0.1 to 10 weight percent, more usually from about 1 to 5 weight percent. The collagen medium will generally be at a concentrate of the base in the range of about 0.0001 to 0.1N. The pH is generally maintained during the course of the reaction in the range of about 10–13, preferably about 12.

Insoluble, fibrillar collagen is preferably used and can be prepared by routine methods. Typically, this can be accomplished with by first mixing with isopropanol (IPA), diethyl ether, hexane, ethyl acetate, or other suitable solvent, and separating the collagen. The pH is typically lowered to about 3, then cooled to about 4° C., and allowed to swell. The resulting slurry may be homogenized until the desired viscosity is attained.

The homogenized slurry is mixed with solvent, agitated, and the pH is raised to about 7. The fibrillar collagen is separated, rinsed with deionized water, and lyophilized. To produce mineralized fibrillar collagen, the purified insoluble collagen fibrils may be homogenized, placed in a reactor where calcium chloride (typically, 0.05 m) and tribasic sodium phosphate (typically, 0.03 m) are introduced at a controlled rate with stirring. Sodium hydroxide is used to adjust pH at 11.0±0.5 as needed during this process. After mineralization, the collagen is rinsed with deionized water or phosphate buffer, combined with the binder and the pH is adjusted within a range of 7.5±1.5. A method of addition of phosphate and calcium ions is described in U.S. Pat. No. 5,231,169.

The calcium phosphate may contain other ions, such as carbonate, chloride, fluoride, sodium or ammonium. The presence of carbonate results in a product having the properties of dahllite (carbonated hydroxyapatite), while fluoride provides a product having the properties of fluoridated apatite. The weight % of carbonate will usually not exceed 10, while the weight of % of fluoride will usually not exceed 2. preferably in the range of 0 to 1. These ions may be present in conjunction with the calcium and/or phosphate source, so long as the ions are compatible and do not result in precipitation in the reagent solutions.

The rate of addition of the calcium and phosphate ions is generally about one hour and no more than about 72 hours in order to achieve the particle size of about 5 microns or less. Generally, the addition period is in the range of about 2 to 18 hours, more usually, in the range of about 4 to 16 hours. Mild temperatures are employed, usually not more than about 40° C., preferably in the range of about 15° to 30° C. The weight ratio of the collagen to calcium phosphate mineral will generally be in the range of about 8:2 to 1:1, and typically will be about 7:3.

Other non-collagenous proteins or factors, such as BMP's, TGF-β, calcitonin, etc., may be included in the matrix by adding to the collagen slurry, prior or subsequent to calcium and phosphate addition. The amounts of such additives will generally be in the range of about 0.0001 to 2 weight % based on the biopolymer used as the matrix, such as collagen. The added protein may combine with the mineral as it forms on the collagen, binding the added protein to the collagen.

The amount of collagen present in the mineralized product will generally be from about 80% to 30%.

Alternatively, the immobilized calcium phosphate particles may be included in the matrix by mixing particles with the binder used to bind the collagen fibrils.

To form a porous, three-dimensional bone grafting matrix, the mineralized collagen fibers are mixed with a binder.

Preferably, purified soluble collagen is used as the binder by first mixing soluble collagen with a solvent, such as isopropanol (IPA), and isolating the collagen. The pH is lowered to about 3.0, then, when the collagen is dissolved, the pH is raised to 5.0 washed twice with the solvent, rinsed with deionized water, sieved, and lyophilized.

Other binders which may be used include, but are not limited to, gelatin, polylactic acid, polyglycolic acid, copolymers of lactic and glycolic acid, polycaprolactone, carboxymethylcellulose, cellulose esters (such as the methyl and ethyl esters), cellulose acetate, dextrose, dextran, chitosan, hyaluronic acid, ficol, chondroitin sulfate, polyvinyl alcohol, polyacrylic acid, polypropylene glycol, polyethylene glycol, water soluble methacrylate or acrylate polymers.

To prepare the porous matrix, the preferred soluble collagen binder is added to a mineralized collagen slurry and blended. Preferably, a proportion of about 10% (wt:wt) soluble to insoluble collagen is used. The pH is adjusted to 7.5±0.5, as needed. When the desired level of blending is achieved, the dispersion is frozen at −20° C. to −80° C.

The frozen slurry is lyophilized. The porous matrix may be cross-linked to enhance physical stability, increase the resorption time of the matrix and ease the handling of the final product. The lyophilized matrix is preferably cross-linked using glutaraldehyde in solution (typically, 0.01%) or vapor. If a solution is used, after removal of excess reagent, the matrix is dehydrated by lyophilization.

The porous matrix may also be formed by filtering the slurry of mineralized collagen fibers and binder to form a web. The dried web may then be cross-linked.

The porous structure may also be achieved by mixing the mineralized collagen fibers, binder and leachable particle (soluble salts, such as sodium chloride) and/or high vapor pressure solids which can be later removed by sublimation. The slurry can be dried, then the leachable or sublimable particles can be removed to form the porous structure. The porous matrix may be cross-linked.

Other benefits of a cross-linked matrix include greater implant residence time and shape retention (no fragmentation of the implant).

Other cross-linking methods and agents may be used, such as formaldehyde, chromium salts, di-isocyanates, carbodiimides, difunctional acid chlorides, difunctional anhydrides, difunctional succinimides, dibromoisopropanol, epichlorohydrin, diepoxides, dehydrothermal cross-linking, UV radiation when dry, or E-beam or gamma radiation in aqueous solution.

Final product sterilization may be accomplished using gamma radiation, E-beam radiation, dry heat or ethylene oxide.

An advantage of the present invention is that the collagen fibrils and the immobilized calcium phosphate mineral form a matrix particularly advantageous for the replacement or augmentation of bone. The matrix maintains its physical integrity for a period of at least about three days after implant and maintains its porosity for a period of about seven to fourteen days after implant into a physiological environment in which bone replacement is occurring. By physical integrity it is meant that the shape and size of the implanted matrix is substantially maintained. This is in contrast to compositions which, immediately or shortly after implant, collapse into an amorphous non-porous mass. It is advantageous that the matrix also maintains its porosity which is important to the bone replacement or augmentation process.

The matrix according to the present invention will eventually biodegrade or be absorbed, so the porosity and physical integrity cannot be maintained beyond that limiting period. This process normally takes on average, about 2 to 12 weeks, and is of course dependent upon the size of the matrix that is implanted. However, as long as the period after which there has been complete absorption or biodegradation of the matrix has not occurred prior to the bone replacement or augmentation process, the rate of biodegradation will be sufficient.

It is an aspect of the present invention that the calcium phosphate minerals, typically present as hydroxyapatite, are immobilized on the matrix, as opposed to being freely mobile throughout the matrix. It has been found that the calcium phosphate mineral according to the present invention are immobilized within the matrix and comprises particles of average diameter less than about five microns. The particle size of a material can alter the biological interactions when implanted which may affect the tissue response to the material. The cellular response can be altered in that phagocytic cells such as giant cells and macrophages are more prominent around particulate materials, frequently forming granulomas. Particles small enough to be phagocytized, approximately 3 to 5 microns or less in size, are taken up by phagocytic cells which further stimulate a localized tissue reaction. For example, it is observed during bone healing that particulate wear debris associated with artificial joints are found in the macrophages of adjacent tissue and is associated with increased bone resorption in animal models in a dose dependent manner ("Macrophage/particle interactions: effect of size, composition, and surface area", Shanbhag AS et al., J. Biomed. Mater. Res. 28(1), 81–90 (1994)). It is thus an advantage of the invention that the immobilized calcium phosphate mineral is released over time as 5 micron or less particles, an ideal size to be taken up by phagocytic cells. It is a further advantage of the invention that any release of the calcium phosphate mineral particles is controlled, which is a result of mineral being immobilized within the matrix. The advantages of the particle size and immobilization are shown in Example III, below.

The bone grafting material has application as an osteoconductive bone grafting material for spinal fusion, filling bone defects, fracture repair and grafting periodontal defects. By combining the subject composition with an osteogenic material, such as autogenous bone or autologous aspirated bone marrow, or osteoinductive bone growth factors, BMP's, calcitonin or other growth factors, bone induction and growth may be further augmented. The matrix may also provide a substrate to which growth factors may bind, so that factors produced by the host or externally introduced can concentrate at the matrix. The subject compositions find application in fracture repair, maxifacial reconstruction, spinal fusion, joint reconstruction, and other orthopedic surgical uses.

The following examples are provided by way of illustration and are not intended to limit the invention in any way.

EXAMPLE I

The mineralized collagen matrix according to the invention is implanted into defects created in the parietal bones of 8 week-old rats. Histological assessments are performed at 14 and 28 days. After 14 days, bone growth from the cut edge of the defect into the collagen matrix is observed. The newly formed woven bone surrounds pieces of the residual matrix and areas of loose connective tissue in which vascularization is evident. By 28 days, significant remodeling had occurred, with osteocytes present throughout the new bone. The connective tissue cavities seen at 14 days diminished in size as bone growth continued.

EXAMPLE II

The calcium phosphate mineralized collagen matrix from Example I was implanted with the addition of bone marrow into mature male New Zealand white rabbits (3.7 to 4.1 kilograms). An incision was made mid-shaft over the anterior-medial surface of the right forearm to expose the radius. A critical defect was created by removing a 1.5 centimeter segment of the radius using a pneumatic drill. Irrigation was provided during osteotomy to minimize overheating and damage to the bone. The defect was filled with the mineralized collagen matrix mixed with bone marrow or autogenous graft. The bone marrow was aspirated from the tibia of the same animal. The autogenous graft was cancellous bone harvested from the iliac crest similar to the current bone augmentation or grafting procedure. Post-surgically, the animals were observed daily, and radio-graphs were taken of the operated radius every two weeks for the first eight weeks and monthly until necropsy at 12 weeks. The rabbits were scheduled to survive for 12 and 24 weeks post-surgery.

At necropsy, the right and left radii were removed and the operated radius was evaluated for gross signs of healing (callus formation and union). The examination included the presence of bone indicating a union or the presence of cartilage, soft tissue or cracks within the defect indicating a possible unstable union.

The radii were then fixed in 10% neutral buffered formalin and processed for histologic and morphometric evaluations.

Radiographs taken at 0, 2, 4, 6, 8, and 12 weeks indicated a robust healing response as early as two weeks and the defect sites continue to improve and remodel towards reconstituting the natural cortices of the radius. The progressive healing observed was consistent between the calcium phosphate collagen matrix treated groups and the autografts control group. There was little difference in radiographic unions between the two cross-linking groups.

In earlier studies, it had been shown that defects left empty or untreated (negative control) contained little or no new bone. In this test the autograft (positive control) formed a stable boney union. The calcium phosphate collagen treated defects which included bone marrow also demonstrated steady bridging with new bone comparable to that seen with autograft.

EXAMPLE III

Comparative Example

A batch of calcium phosphate mineral was prepared without the addition of collagen. The mineral was harvested, washed, and lyophilized to a dry powder. Infrared spectroscopy showed it to be hydroxyapatite in character.

An admix matrix was made by mixing insoluble fibrillar collagen fibers with soluble collagen in a 9/1 weight ratio, at a total solids of 4 wt %. The slurry was mixed by hand and the free mineral was added to make up 25 wt % of the total solids. The slurry was poured into 2 inch square Teflon molds to a depth of approximately 5 mm, frozen at −80 degrees C., and lyophilized. The dry matrix was cross-linked using glutaraldehyde for 30 minutes, washed, and re-lyophilized. The resultant matrix was about 4 mm in thickness, and punch samples of 8 mm diameter were made from the matrix for implantation. For comparison, a recently made batch of mineralized collagen (immobilized mineral), with an ash content of 28 wt % was used for 8 mm diameter punched implants.

The implants were placed subcutaneously in the thoracic fascia, with two implant materials of the same type bilaterally in four rats at each implantation time point of 3, 7, and 14 days. At necropsy, the implants were scored for tissue reaction, and tissue blocks taken for histology. H&E stained sections of the implant and surrounding tissue were examined for each animal at each time point to characterize tissue reaction and integration.

OBSERVATIONS AT NECROPSY

|  | Admix (non-immobilized mineral) | Mineralized collagen |
| --- | --- | --- |
| 3 days | Surrounding tissue clear, implants mushy | Surrounding tissue clear, implants soft |
| 7 days | Surrounding tissue clear, implants soft, but feel thickened | Surrounding tissue clear, implants soft to firm |
| 14 days | Surrounding tissue inflamed, implants firm but feel thickened | Surrounding tissue clear, implants firm |

The clinical observations at necropsy indicate a much greater inflammatory response and degradative effect on the admix formulation as compared to the immobilized mineralized collagen in the rat subcutaneous implant model. Observations describe a mushy implant at three days. At seven and 14 days, a thickened implant is observed, probably due to the dramatic fibrous capsule response of the admix formulation as observed histologically. The formulation with immobilized mineral in comparison demonstrated clear surrounding tissue and normal implant appearance at all three time points.

Histologic examination showed that the admix formulation resulted in a high level of both acute and chronic inflammation as demonstrated by the late (14 day) PMN activity and early (3 day) giant cell activity. The giant cells indicate that phagocytic activity is being organized probably in response to the large amount of loosely associated particles of mineral. Fibroblastic invasion is still observed and tissue necrosis was not evident.

In contrast, the formulation with mineral particles immobilized on the collagen fibers demonstrates a more typical implant-tissue reaction. At the three day time point, acute inflammation is observed which rapidly subsides to a more chronic implant reaction at seven days, with only moderate inflammation while fibroblastic invasion and neovascularization is occurring at the implant periphery. At 14 days, signs of increased inflammation are visible, perhaps indicative of additional mineral release from the collagen fibers due to collagen degradation.

The admix formulation of the collagen and hydroxyapatite mineral components demonstrates a significant acute inflammatory response in subcutaneous rat implants. The immobilization of the mineral component in the mineralized collagen composition appears to reduce the bioavailability of the mineral, reducing inflammation while continuing to support tissue integration during wound healing.

What is claimed is:

1. A method of making a biodegradable porous bone grafting matrix which maintains physical integrity for a period of at least about 3 days after implant and its porosity for about 7–14 days after implant into a physiological environments in which bone replacement is occurring, comprising the steps of:

(a) forming a dispersion comprising a biodegradable water-insoluble biopolymer, a water-soluble binder, and particulate calcium phosphate mineral immobilized by said binder or biopolymer;

(b) forming said dispersion into a porous matrix;

(c) cross-linking said porous matrix.

2. A method according to claim 1 wherein said step (b) comprises lyophilizing said dispersion.

3. A method according to claim 1 wherein said dispersion further comprises leachable particles and said step (b) comprises drying said dispersion and leaching said particles to form said matrix.

4. A method according to claim 1 wherein said dispersion further comprises sublimable particles and said step (b) comprises drying said dispersion and subliming said particles to form said matrix.

5. A method according to claim 1 wherein said biodegradable water-insoluble biopolymer comprises mineralized collagen fibrils containing about 30–80% by weight of collagen.

6. A method according to claim 1 wherein said binder comprises soluble collagen.

7. A method according to claim 1 wherein said mineral comprises hydroxyapatite.

8. A method according to claim 1 wherein said mineral consists of particles of a diameter of about five microns or less.

* * * * *